United States Patent
Olah et al.

(10) Patent No.: US 7,378,561 B2
(45) Date of Patent: May 27, 2008

(54) METHOD FOR PRODUCING METHANOL, DIMETHYL ETHER, DERIVED SYNTHETIC HYDROCARBONS AND THEIR PRODUCTS FROM CARBON DIOXIDE AND WATER (MOISTURE) OF THE AIR AS SOLE SOURCE MATERIAL

(75) Inventors: George A. Olah, Beverly Hills, CA (US); Robert Aniszfeld, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 11/780,171

(22) Filed: Jul. 19, 2007

(65) Prior Publication Data

US 2008/0039538 A1    Feb. 14, 2008

Related U.S. Application Data

(60) Provisional application No. 60/837,273, filed on Aug. 10, 2006.

(51) Int. Cl.
C07C 29/51 (2006.01)
C07C 29/15 (2006.01)
C07C 29/132 (2006.01)

(52) U.S. Cl. ...................... 568/885; 568/884

(58) Field of Classification Search .......... 568/885, 568/884
See application file for complete search history.

(56) References Cited

U.S. PATENT DOCUMENTS 4,243,613 A    1/1981  Brockhaus et al. ......... 568/482
4,762,528 A    8/1988  Reichl ........................ 44/51
5,364,887 A   11/1994  Konig et al. ............... 518/713
5,928,806 A    7/1999  Olah et al. ................. 429/13

FOREIGN PATENT DOCUMENTS

| EP | 1 180 511 A1 | 2/2002 |
| FR | 2 543 946 A1 | 10/1984 |
| JP | 59-216839 | 12/1984 |
| WO | WO 2005/037746 A1 | 4/2005 |

OTHER PUBLICATIONS

Ashby, E.C. et al., "Concerning The Formation Of Hydrogen In Nuclear Waste. Quantitative Generation Of Hydrogen Via A Cannizzaro Intermediate," J. Am. Chem. Soc., vol. 115, pp. 1171-1173 (1993).

*Primary Examiner*—Elvis O. Price
(74) *Attorney, Agent, or Firm*—Winston & Strawn LLP

(57) ABSTRACT

A method for producing methanol and dimethyl ether using the air as the sole source of materials is disclosed. The invention relates to a method for separating the water (i.e., the moisture in the air) and carbon dioxide content of atmospheric air for their use in the subsequent production of methanol, dimethyl ether and derived synthetic hydrocarbons as products. The method includes the conversion of carbon dioxide and water under conditions sufficient to produce methanol and/or dimethyl ether. Methanol and/or dimethyl ether can be used as fuel or fuel additives or further converted to synthetic hydrocarbons and their products. Carbon dioxide is captured on a suitable absorbent, preferentially polyethyleneimine supported on nano-structured fumed silica. The process can also involve hydrogenation with hydrogen produced by electrolysis of water obtained from the air or from any other water source. Methanol can be dehydrated to produce dimethyl ether or further processed to produce synthetic hydrocarbons, polymers, and products derived from them by other known methods.

13 Claims, No Drawings

METHOD FOR PRODUCING METHANOL, DIMETHYL ETHER, DERIVED SYNTHETIC HYDROCARBONS AND THEIR PRODUCTS FROM CARBON DIOXIDE AND WATER (MOISTURE) OF THE AIR AS SOLE SOURCE MATERIAL

This application claims the benefit of U.S. Patent No. 60/837,273 filed Aug. 10, 2006, the entire content of which is expressly incorporated herein by reference thereto.

FIELD OF THE INVENTION

The invention discloses to the conversion of carbon dioxide and water (moisture) of the air as the source material to methanol, dimethyl ether, derived synthetic hydrocarbons and products there from.

BACKGROUND OF THE INVENTION

Fossil fuels are a major source of energy today. They are used to generate heat and electricity and are the source materials for transportation fuels. Fossil fuels also serve as raw materials for various hydrocarbons and their derived products essential to our everyday life. Combustion of fossil fuel, however, produces carbon dioxide that contributes to global warming adversely affecting the environment. In addition, fossil fuel reserves are on a decline.

As an alternative to the declining reserves of fossil fuels, the use of methanol as a raw material for producing synthetic hydrocarbons and fuels has been suggested. Carbon dioxide has also been suggested as an alternative source of raw material (see, e.g., U.S. Pat. No. 5,928,806). It would be highly advantageous to utilize carbon dioxide, considering its virtually inexhaustible supply particularly if it could be economically captured and recycled from the atmosphere.

Carbon dioxide is present in high concentrations in the flue gases of fossil fuel-burning power plants and other various industrial exhausts. It also frequently accompanies natural gas. Many natural gas sources contain significant amounts (as much as 50% or more) of carbon dioxide. To mitigate carbon dioxide emissions and their adverse effects on the global climate, it considered to capture carbon dioxide from industrial exhausts and sequester the captured carbon dioxide in subterranean cavities or under the sea. However, sequestration does not provide a permanent solution because of its high cost and a potential for carbon dioxide leakage. Carbon dioxide is volatile and can eventually leak into the atmosphere. Inadvertent leaks of carbon dioxide can be greatly accelerated by earthquakes or other natural phenomena, and would have a catastrophic impact.

Furthermore, while it is of critical importance to curtail carbon dioxide emissions into the atmosphere, recent studies suggest that this alone will not be sufficient to reverse the damage that has already occurred. Thus, in addition to having a method for safely disposing carbon dioxide so that it does not enter the atmosphere, it would be of great benefit to also be able to remove carbon dioxide from the atmosphere to more quickly reverse the problem of carbon dioxide buildup in the atmosphere. It also would be beneficial to conduct chemical recycling of atmospheric carbon dioxide as this would provide an inexhaustible carbon source for producing fuels and synthetic hydrocarbons while at the same time mitigating global climate change that is caused or affected by the increase of carbon dioxide in the atmosphere.

SUMMARY OF THE INVENTION

The invention relates to a method for producing methanol from atmospheric air, which comprises removing water from atmospheric air by dehumidification of moisture therefrom; obtaining hydrogen from the removed water by catalysis or other means of cleavage; obtaining carbon dioxide by absorption or adsorption from the dehumidified atmospheric air; and converting the carbon dioxide thus obtained by suitable methods of reduction and hydrogenation under conditions sufficient to produce methanol. In this process, the carbon dioxide, water, and derived hydrogen are obtained solely from atmospheric air as the source material using any necessary form of energy.

The water (i.e., the moisture in the air) and carbon dioxide content of atmospheric air are separated for use in the subsequent production of methanol, dimethyl ether and derived synthetic hydrocarbons as products. Using air as the source material provides an inexhaustible supply of the starting materials necessary to make such products. The method comprises of the conversion of carbon dioxide and water under conditions sufficient to produce methanol and/or dimethyl ether. Methanol and/or dimethyl ether can be used as fuel or fuel additives or further converted to synthetic hydrocarbons and their products.

The water can be obtained by dehumidifying the air while the carbon dioxide can be obtained by adsorbing atmospheric carbon dioxide onto a suitable adsorbent and then treating the adsorbent to release the adsorbed carbon dioxide. The carbon dioxide can be obtained from the air after removal of its moisture (i.e. water content).

In one embodiment, methanol is produced by catalytic hydrogenation of carbon dioxide, wherein the hydrogen used in the hydrogenation is obtained by electrolysis of pure water obtained from the air. In another embodiment, methanol is produced by reducing the carbon dioxide under conditions sufficient to obtain carbon monoxide, reacting the carbon monoxide with methanol under conditions sufficient to obtain methyl formate, and catalytically hydrogenating the methyl formate under conditions sufficient to produce twice the amount of used methanol.

Methanol produced according to the invention can be further processed to any desired derivative or derived compounds. For example, methanol can be dehydrated to produce dimethyl ether, both of which are valuable transportation fuels. Both methanol or dimethyl ether can also be further treated under conditions sufficient to form compounds such as ethylene and propylene. Ethylene and propylene can be converted to higher olefins, synthetic hydrocarbons, aromatics, or related products, and therefore are useful as a feedstock for chemicals or transportation fuel.

In a further embodiment, methanol, together with nitrogen also separated from the air, and used to produce ammonia or ammonia salts, are used for microbiological production of proteins.

DETAILED DESCRIPTION OF PREFERRED EMBODIMENTS

The invention relates to the use of atmospheric air as the sole source for the production of methanol and compounds derived from methanol, such as dimethyl ether, which can then be used for energy storage and transportation, production of transportation fuels, and derived synthetic hydrocarbon products.

In one embodiment, the invention relates to the use of the air, which contains a small but significant amount of carbon dioxide and a more significant amount of water (i.e., water vapor) as the sole source material for producing methyl alcohol and/or dimethyl ether. The air has a low $CO_2$ content (0.037%) and a relatively high moisture content (2-6%, depending on the conditions, including temperature, pressure, humidity, etc.). After dehumidification of the air to remove its water content, any process for capturing and isolating $CO_2$ from the air, whether by absorption or adsorption with a sorbent, membrane separation, or any other technique can advantageously be used in this invention.

As water is frequently not available in many locations and/or may need extensive purification, distillation etc. before it can be used for generating hydrogen, the pure water obtained from the atmosphere is hence directly suitable to be used as a hydrogen source.

$CO_2$ can be isolated from the air by any suitable means, including membrane separation or with any sorbent device or material. An efficient process for capturing and reversibly adsorbing $CO_2$ from a gas mixture using a nano-structure supported absorbent such as fumed silica is disclosed in co-pending U.S. Provisional Patent Application No. 60/837,274 filed Aug. 10, 2006, the entire content of which is incorporated herein by reference thereto. After carbon dioxide is captured, it can be released readily through heating and/or reduced pressure for use in the reactions described herein.

Water (i.e., the moisture content of the air) can be isolated from the air by any suitable means. The water isolated from the air is of high purity and can be utilized directly in any desired manner as a source for hydrogen production catalytically or electrochemically. The hydrogen so obtained can be used in the hydrogenative conversion of $CO_2$ to methanol.

$CO_2$ and $H_2O$ thus can be obtained from atmospheric air as common source material and used to produce methanol or dimethyl ether according to the processes described in U.S. Pat. No. 5,928,806 and co-pending U.S. patent application Ser. No. 11/402,050, the entire content of each of which is incorporated herein by reference thereto. U.S. Pat. No. 5,928,806 describes a method of reducing carbon dioxide and water to form oxygenated hydrocarbons such as methyl alcohol, methyl formate, formaldehyde or formic acid by, for example, providing carbon dioxide, water and electrical energy to a reduction zone such that the carbon dioxide and water react to form oxygen and an oxygenated hydrocarbon or a mixture of oxygenated hydrocarbons. U.S. patent application Ser. No. 11/402,050 provides methods for converting $CO_2$ to methanol by catalytic hydrogenation and discloses that hydrogen used in the catalytic hydrogenation can be obtained from any suitable source, including electrolysis of water. This application discloses reducing carbon dioxide to produce a reaction mixture containing formic acid with concomitant formation of formaldehyde and smaller amounts of methanol. It is followed by a treatment to convert the formaldehyde and formic acid to methanol. Besides using Canizzaro-Tischenko type chemistry to convert formaldehyde to methanol, the amount of methanol produced can be increased by reacting the formaldehyde with formic acid (as a hydrogen source) to synthesize methanol. Alternatively, formic acid can be reacted with methanol to form methyl formate, which upon catalytic hydrogenation will give twice the amount of methanol. Through another route, carbon dioxide can be used to generate carbon monoxide through a high temperature reaction with carbon and then reacting the carbon monoxide so produced with methanol to form methyl formate, followed by catalytic hydrogenation to methanol. The energy required for the process of separating $CO_2$ and water from the air, and of subsequently converting $CO_2$ and hydrogen to methanol or dimethyl ether, can be provided by any conventional or alternative source, including atomic, geothermal, solar, and wind energy.

Methanol and dimethyl ether produced from atmospheric $CO_2$ and $H_2O$ according to the invention are convenient to store and transport. Methanol is an excellent transportation fuel and can be easily treated to produce synthetic hydrocarbons and derived materials. It can also be converted into dimethyl ether, (which is produced by dehydration of methanol) or to dimethyl carbonate. Dimethyl carbonate can be produced by oxidative carbonylation of methanol. According to the invention described herein, all these useful fuels can be produced solely from the air.

Methanol, dimethyl ether, and synthetic hydrocarbon products and compounds derived from them are useful as convenient and safely storable energy sources and fuels, as well as useful starting materials for various chemicals, synthetic hydrocarbons and related products. Methanol and/or dimethyl ether can be converted in the presence of an acidic-basic or zeolitic catalysts to produce ethylene and/or propylene, which are useful to produce polymers, and as feedstock for other synthetic hydrocarbons, derived materials and chemicals including transportation fuels. For example, ethylene and propylene can be hydrated to form ethanol and propanol, respectively, they can be converted to higher olefins, polyolefins, varied synthetic hydrocarbons, or aromatic compounds, as well as products produced from these compounds.

As all of these reactions are generally known to skilled practitioners, there is no need to recite detailed reaction conditions herein. The skilled practitioner is well aware of conditions sufficient to achieve or produce the desired products using the starting materials derived from the atmosphere as the only source material as disclosed herein.

Methanol can also be used as a food source for single-cell organisms or microorganisms to produce proteins, e.g., single cell proteins, in aqueous media in the presence of nitrogen-containing nutrient salts, by utilizing nitrogen from the air. Thus, the invention also provides a method for producing nitrogen-containing alimentary products such as proteins by utilizing $CO_2$, $H_2O$, and $N_2$ obtained solely from the air. In this embodiment, the atmospheric air is used not only as a renewable carbon source (i.e., carbon dioxide) and a source of hydrogen (derived from the air's moisture content) but also as a source of nitrogen for producing nitrogen-containing proteins. Single cell proteins thus produced can be used for any desired purpose including human or animal alimentation.

The use of the air as the sole-source material in the conversion of $CO_2$ and $H_2O$ to methanol or dimethyl ether according to the invention due to its universal availability on earth provides unique and significant advantages by enabling universal direct utilization of the air, available to everybody to produce essential fuels and hydrocarbon products. Whereas water is abundant on earth, clean water is not available in many areas. Seawater desalination is a possible, although expensive, way of obtaining clean water. In arid areas, water must be brought in from outside and sometime distant locations. The clean water obtained from the moisture of the air is thus a useful and even economical by-product of atmospheric $CO_2$ isolation. By using the air as the only source material to produce methanol and derived products, the invention provides an inexhaustible and universally available source of $CO_2$ and $H_2O$ everywhere on earth. It thus provides a basis for fuels and materials needed to replace increasingly diminishing reserves of fossil fuels.

The process is also advantageous in that it mitigates global climate change due to increased concentration of $CO_2$ in the atmosphere while effectively utilizing $CO_2$ and water in the atmosphere to produce essential fuels and products.

EXAMPLES 1

The moisture content of the air is removed by any convenient and applicable method of dehumidification using appropriate cooling and absorption techniques. After removal of the bulk atmospheric moisture, the treated air is passed through an adsorbing systems consisting of a suitable chemical absorbent, known to efficiently absorbing carbon dioxide.

EXAMPLE 2

Clean water removed by dehumidification of air and used for electrolytic generation of hydrogen.

EXAMPLE 3

Carbon dioxide absorbed or adsorbed according to example 1 is subsequently desorbed by heating and/or application of decreased pressure and then converted chemically to methanol.

EXAMPLE 4

Absorbent system for removal carbon dioxide from the dehumidified air consisting of preferentially a polyethyleneimine polymer or other polyamino groups containing polymers.

EXAMPLE 5

Absorbent used in example 4 rendered of significantly increased activity by supporting on fumed silica, alumina or other suitable supports of nano-structured nature with high surface activity.

What is claimed is:

1. A method for producing methanol from atmospheric air, which comprises:
    removing water from atmospheric air by dehumidification of moisture therefrom;
    obtaining hydrogen from the removed water by catalysis or other means of cleavage;
    obtaining carbon dioxide by absorption or adsorption from the dehumidified atmospheric air; and
    converting the carbon dioxide thus obtained by suitable methods of reduction and hydrogenation under conditions sufficient to produce methanol;
    wherein the carbon dioxide, water, and derived hydrogen are obtained solely from atmospheric air as the source material using any necessary form of energy.

2. The method according to claim 1, wherein all water for the reaction is obtained by dehumidifying of the air.

3. The method according to claim 2, wherein the carbon dioxide is separated from the air subsequent to dehumidification.

4. The method according to claim 1, wherein the absorbent is a polyamino containing polymer deposited on a nano-structured high surface area support.

5. The method according to claim 4, wherein the polyamino containing polymer is a polyethyleneimine and the support is fused silica or alumina.

6. The method according to claim 3, wherein the carbon dioxide is obtained by capturing atmospheric carbon dioxide on a sorbent that is subsequently desorbed by treating the sorbent to release the captured carbon dioxide therefrom.

7. The method according to claim 6, wherein the sorbent is treated with sufficient heating, reduced pressure, vacuum, gas purge, or a combination thereof to release the captured carbon dioxide.

8. The method according to claim 7, wherein the hydrogen is obtained by electrolysis or catalytic or thermal cleavage of the water that is removed from atmospheric air.

9. The method according to claim 8, wherein methyl alcohol or dimethyl ether is produced from the carbon dioxide and water that is obtained from the air.

10. The method according to claim 1, which further comprises reducing the carbon dioxide under conditions sufficient to form carbon monoxide, reacting the carbon monoxide with methanol under conditions sufficient to obtain methyl formate, and catalytically hydrogenating the methyl formate under conditions sufficient to produce exclusively methanol.

11. The method according to claim 1, which further comprises converting methanol under conditions sufficient to produce dimethyl ether.

12. The method according to claim 11, which further comprises reacting the dimethyl ether in the presence of an acidic-basic or zeolitic catalyst under conditions sufficient to form ethylene and/or propylene.

13. The method according to claim 12, which further comprises converting ethylene or propylene under conditions sufficient to produce varied synthetic hydrocarbons, derived chemicals, polymers, and products produced from them.

* * * * *